United States Patent
Chen et al.

(10) Patent No.: US 10,317,379 B2
(45) Date of Patent: Jun. 11, 2019

(54) HIGH PERFORMANCE LIQUID CHROMATOGRAPHY WITH UV-VISIBLE DETECTION

(71) Applicant: Academia Sinica, Taipei (TW)

(72) Inventors: Chung-Hsuan Chen, Taipei (TW); Chen-Yu Hsieh, Taipei (TW); Jung-Lee Lin, Taipei (TW)

(73) Assignee: Academia Sinica, Taipei (TW)

( * ) Notice: Subject to any disclaimer, the term of this patent is extended or adjusted under 35 U.S.C. 154(b) by 228 days.

(21) Appl. No.: 14/551,050

(22) Filed: Nov. 23, 2014

(65) Prior Publication Data

US 2015/0143880 A1 May 28, 2015

Related U.S. Application Data

(60) Provisional application No. 61/908,159, filed on Nov. 24, 2013.

(51) Int. Cl.
G01N 21/33 (2006.01)
G01N 30/02 (2006.01)
G01N 30/74 (2006.01)

(52) U.S. Cl.
CPC ............ *G01N 30/74* (2013.01); *G01N 21/33* (2013.01); *G01N 2030/027* (2013.01)

(58) Field of Classification Search
CPC ... G01N 2030/027; G01N 30/74; G01N 21/33
See application file for complete search history.

(56) References Cited

U.S. PATENT DOCUMENTS

| | | | | |
|---|---|---|---|---|
| 4,883,409 A | * | 11/1989 | Strohmeier | F04B 11/00 210/101 |
| 5,231,462 A | * | 7/1993 | Dschen | G01J 3/433 356/328 |
| 6,559,941 B1 | * | 5/2003 | Hammer | G01J 3/04 356/319 |
| 7,489,400 B1 | * | 2/2009 | He | G01J 3/02 356/369 |
| 2007/0182962 A1 | * | 8/2007 | Bearman | G01J 3/02 356/328 |

(Continued)

FOREIGN PATENT DOCUMENTS

WO     2011161481 A1     12/2011

OTHER PUBLICATIONS

Ewa Lipczynska-Kochany and James R. Bolton, "Flash Photolysis/High-Performance Liquid Chromatography Method for Studying the Sequence of Photochemical Reactions: Direct Photolysis of Phenol", Published 1992 in Environmental Science Technology vol. 26, pp. 2524-2537.*

(Continued)

*Primary Examiner* — Justin Seo
*Assistant Examiner* — John M Royston
(74) *Attorney, Agent, or Firm* — Eckman Law Group

(57) ABSTRACT

Apparatus and methods for high performance liquid chromatography. The apparatus includes a preparation loop comprising two linear stepping pumps, a sample loop comprising a sample injector, a chromatography column, and a detector device. The detector device can include a flash lamp, a flow cell, and a light sensor comprising an entrance slit, a grating; and a charge-coupled device array.

8 Claims, 3 Drawing Sheets

(56) References Cited

U.S. PATENT DOCUMENTS

| | | | | |
|---|---|---|---|---|
| 2007/0283746 A1* | 12/2007 | Gerhardt | ............... | G01N 30/22 |
| | | | | 73/61.56 |
| 2009/0145485 A1* | 6/2009 | Smith | ................... | B01F 5/0646 |
| | | | | 137/2 |
| 2010/0230355 A1* | 9/2010 | Kerr | ................... | B01D 15/1892 |
| | | | | 210/657 |
| 2011/0050965 A1* | 3/2011 | Uzumaki | ............. | H04N 5/2256 |
| | | | | 348/241 |
| 2012/0228519 A1* | 9/2012 | Gilmore | ............... | G01N 21/645 |
| | | | | 250/459.1 |
| 2012/0308409 A1* | 12/2012 | Levine | ................. | G01F 23/603 |
| | | | | 417/274 |
| 2013/0015138 A1* | 1/2013 | Schlake | ............... | B01D 15/165 |
| | | | | 210/656 |

OTHER PUBLICATIONS

Patel, Electrokinetic pumping of liquid propellants for small satellite microthruster applications, Sensors and Actuators B 132 (2008) 461-470.

Macnair, Ultrahigh-Pressure Reversed-Phase Liquid Chromatography in Packed Capillary Columns, Anal. Chem. 1997, 69, 983-989.

* cited by examiner

HIGH PERFORMANCE LIQUID CHROMATOGRAPHY WITH UV-VISIBLE DETECTION

BACKGROUND OF THE INVENTION

High performance liquid chromatography (HPLC) is one of the most important analytical techniques. HPLC techniques are widely applied in chemistry, medical and pharmaceutical uses, environmental and food sciences, and many other fields.

Liquid chromatography employs a liquid as the carrier for analyte samples. The carrier or mobile phase passes through a stationary phase composed of particles packed in a tube or column. In a conventional HPLC, the particles can be about 7 um in size.

HPLC can be applied to analyte mixtures or species which can be dissolved in water, as well as polymers dissolved in organic solvents.

Recently, new HPLC-related techniques have been developed with improved means of detection. For example, Ultrahigh Pressure Liquid Chromatography (UPLC), Rapid Resolution Liquid Chromatography (RRLC), Ultrafast Liquid Chromatography (UFLC), Rapid Separation Liquid Chromatography (RSLC), and Fast Protein Liquid Chromatography (FPLC).

A drawback of conventional liquid chromatography methods and systems is the difficulty in combining the liquid chromatography apparatus with a mass spectrometer apparatus or other large, conventional analyte detection systems. A liquid chromatography apparatus having a large mass and size is difficult to use in combination with a mass spectrometer that is also typically large.

Further, in medical and health care settings, it would be desirable to have a small and efficient liquid chromatography apparatus so that certain measurements can be done on-site in a patient clinic, rather than being carried out in a larger facility such as a medical center or hospital.

Moreover, for environmental measurements that should be performed in the field or at remote locations such as a rainforest, a geological location such as a volcano, or in a spacecraft or extraterrestrial location, it can be required to have a small and efficient liquid chromatography apparatus. Such a device would allow detection of analytes, chemicals, contaminants or other species at their source.

Another drawback of conventional liquid chromatography methods and systems is the use of a photomultiplier as a light sensor. When a photomultiplier is used as a light sensor, a monochromator and mirrors are generally required to isolate wavelengths of light from the sample.

On the other hand, it is desirable to have a liquid chromatography apparatus that can simultaneously and efficiently detect a range of wavelengths of light.

A further drawback of conventional liquid chromatography methods and systems is in using screw-operated pump heads for liquid transport, which have large mass.

There is a continuing need for a liquid chromatography apparatus having a detector device that can measure a range of wavelengths of light simultaneously. There is also a need for a liquid chromatography apparatus that can provide efficient pumping with less mass. And there is a long standing need for efficient liquid chromatography methods and systems for use with other detection systems, as well as for making measurements in the field.

BRIEF SUMMARY

This invention relates to the fields of liquid chromatography and analyte detection. More particularly, this invention relates to methods and devices for high performance liquid chromatography for efficiently generating chromatograms of analytes with UV-visible and other methods of detection, as well as for reducing the mass requirements of a liquid chromatography apparatus to enhance utilization in several fields.

This invention provides methods and devices for high performance liquid chromatography for efficiently generating chromatograms of analytes with UV-visible and other methods of detection, as well as for reducing the mass requirements of a liquid chromatography apparatus to enhance utilization in several fields.

Embodiments of this invention include a liquid chromatography apparatus having a detector device that can measure a range of wavelengths of light simultaneously. A liquid chromatography apparatus of this invention can provide efficient pumping with less mass.

Embodiments of this invention include:
A liquid chromatography apparatus comprising:
   a preparation loop comprising two linear stepping pumps;
   a sample loop comprising a sample injector;
   a chromatography column; and
   a detector device comprising:
      a flash lamp:
      a flow cell; and
      a light sensor comprising:
         an entrance slit;
         a grating; and
         a charge-coupled device array.

The apparatus above, wherein the grating is an etched silicon light diffraction grating having convex shape for focusing diffracted light.

The apparatus above, wherein the chromatography column is selected from an adsorption, a partition, an ion exchange, an affinity, and a size exclusion retention column.

The apparatus above, wherein the preparation loop can be operated in either isocratic or differential pumping modes.

The apparatus above, wherein the detector device has a scan range of from 230 nm to 800 nm.

The apparatus above, wherein the light sensor is a UV-Visible light sensor.

The apparatus above, wherein the stepping pumps have a minimum step of 0.8 nanoliter.

The apparatus above, wherein the flash lamp is a xenon-based flash lamp.

The apparatus above, wherein the flash lamp is operated with a duty cycle of 50% or less at a power of 2 Watt.

The apparatus above, further comprising a microcomputer controller configured to synchronize the operation of the flash lamp to the operation of the charge-coupled device array.

The apparatus above, wherein the flow cell is an HPLC flow cell.

The apparatus above, wherein the liquid chromatography apparatus has a total volume of less than 10 L.

A method for performing liquid chromatography, the method comprising:
   providing analytes in a carrier liquid;
   step-pumping the carrier liquid through a chromatography column to separate the analytes;
   detecting the separated analytes with a detector device comprising a flash lamp and a UV-Visible light sensor comprising a grating and a charge-coupled device array.

The method above, wherein the grating is an etched silicon light diffraction grating having convex shape for focusing diffracted light.

The method above, wherein the chromatography column is selected from an adsorption, a partition, an ion exchange, an affinity, and a size exclusion retention column.

The method above, wherein the detector device has a scan range of from 230 nm to 800 nm.

The method above, wherein the step-pumping has a minimum step of 0.8 nanoliter.

The method above, wherein the flash lamp is operated at a power of 2 Watt.

The method above, further comprising operating a microcomputer controller to synchronize the operation of the flash lamp to the operation of the charge-coupled device array.

The method above, further comprising focusing diffracted light from the grating onto the charge-coupled device array.

BRIEF DESCRIPTION OF THE DRAWINGS

FIG. 1 shows a schematic of an embodiment of a liquid chromatography apparatus of this invention. The liquid chromatography apparatus can include two or more linear stepping pumps 10, pressure transducers 20, a flow meter 30, a solvent mixer 35, an actuated carrier valve 40, an actuated sample valve 50, a sample injector 60, carrier reservoirs 70, a detector device 80, a column 90, and a microcomputer controller.

FIG. 2 shows a schematic of an embodiment of a detector device 80 of this invention. The detector device can include a flash lamp 110, light fibers 120, a flow cell 130, and a UV-Vis light sensor 140. The UV-Vis light sensor 140 can include an entrance slit 150, a grating 160, and a CCD array 170.

FIG. 3 shows a chromatogram of a sample of MyoGlobin obtained with an HPLC apparatus of this invention. The chromatogram shows retention time versus absorbance and was obtained with UV-Vis absorbance at 400 nm wavelength. The HPLC apparatus of this invention had a total volume less than 10 L and was operated with less than 150 Watt overall power consumption.

DETAILED DESCRIPTION OF THE INVENTION

Figure 1:
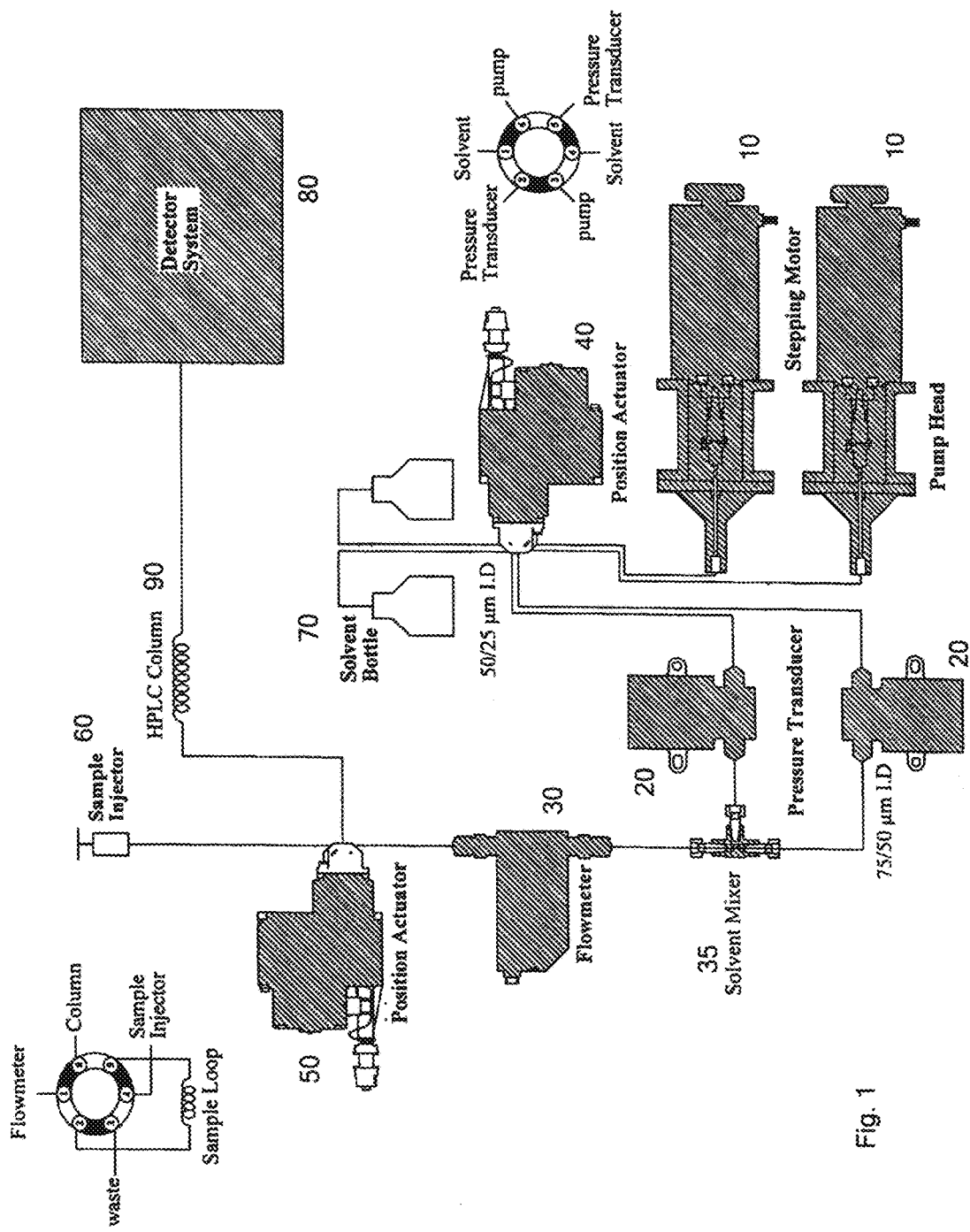
FIG. 1.

Embodiments of this invention provide apparatuses and methods for high performance liquid chromatography. The high performance liquid chromatography apparatus of this invention can provide rapid detection and separation of a complex mixture of analytes.

An HPLC apparatus of this disclosure can have one or more pumps, pressure and flow sensors, switch valves, a column used to separate an analyte mixture, and a detector to analyze samples of analytes.

In some embodiments, a liquid chromatography apparatus of this invention can have one or more pumps, a flow control feedback system, an analyte column, and a detector device.

In some embodiments, an analyte column can have many small particles packed inside forming a stationary phase. Mixtures of analytes can be separated by passing the mixture in a mobile phase through the stationary phase of the column. Different analytes will require different retention times to pass through the column. A separated or purified sample can be generated at the end of column.

Embodiments of a liquid chromatography apparatus of this invention can employ columns for adsorption, partition, ion exchange, affinity, and size exclusion retention.

In some embodiments, a liquid chromatography apparatus of this invention can have a reservoir for a carrier liquid, and a chromatography column in fluid communication with the reservoir.

Embodiments of this invention include a liquid chromatography apparatus that can provide a continuous and stable flow of carrier solvent through the column. The continuous and stable flow of carrier can provide the ability to separate and detect individual analytes.

In certain embodiments, this invention includes a liquid chromatography apparatus that can provide a continuous and stable flow of analytes and carrier so that quantitative measurements of analytes can be performed.

In some aspects, an HPLC apparatus of this invention can have a flow control system. A flow control system can have one or more pressure transducers that feed back to the one or more pumps to maintain a constant pressure in the column.

In certain embodiments, a flow control system can have a flow meter that feeds back to a pump to maintain a constant flow speed in the column.

In certain embodiments, an HPLC apparatus of this invention can operate in either isocratic or differential pumping modes.

In some embodiments, the carrier solvent can be driven by a single mechanical pump in isocratic pumping mode. In isocratic pumping, the composition of the mobile phase may remain constant.

In further embodiments, the carrier solvent can be driven by two mechanical pumps in differential pumping mode. In differential pumping, the composition of the mobile phase varies during acquisition of an HPLC chromatogram to improve resolution and separation. In differential pumping, different solvents can be pumped and mixed at different speeds.

In some aspects, the apparatus of this disclosure maintains a constant pumping speed. A pressure transducer and a flow sensor can be used to provide mechanical pump feedback to maintain a constant pumping speed using a microcomputer.

In certain embodiments, an HPLC apparatus of this invention can have one or two pump heads each having a single piston. A pump head can have a sapphire piston and a stainless steel pump head.

An example of a single piston pump is an DRL42PB2-04 (Oriental Motors).

In another aspect, a liquid chromatography apparatus of this invention can have one or two linear stepping motors to operate the pump heads. A linear stepping motor advantageously provides more efficient pumping as compared to a screw-driven stepping motor. The use of linear stepping motors can reduce power consumption, as well as reduce the required size of the corresponding pump head and maintain constant pumping speeds.

In some embodiments, the pumping step or resolution can be 0.8 nanoliter (nl).

The mass flow rate of an HPLC of this disclosure can be from nanoliters/min to microliters/min. In some embodiments, the mass flow rate of an HPLC of this disclosure can be from 1 nL/min to 20 uL/min.

The pressure in an HPLC of this disclosure can be from 200 to 500 Bar.

An HPLC of this disclosure can include an injector which introduces the sample into the flowing carrier. The volume of a sample for an HPLC of this disclosure can be from 1 to 20 microliters.

In some embodiments, this invention provides a multi-wavelength UV-visible detector device for high performance liquid chromatography.

A detector device of this invention can include a flash lamp, a flash lamp controller, a flow cell, and a UV-Visible light sensor.

An example of a flow cell is an HPLC flow cell.

In some aspects, the flash lamp can be a miniature xenon based flash lamp (e.g., Excelitas).

In certain aspects, an apparatus of this invention includes a lamp controller that synchronizes the illumination of the lamp to the operation of the light sensor. By synchronizing the illumination of the lamp to the operation of the light sensor, an apparatus of this disclosure can provide high light intensity and reduce the electrical power required to operate the apparatus for the detection of analytes.

For example, in a detector device of this disclosure, a flash lamp can be operated with a pulsed duty cycle of 50% or less. A lamp controller can be used to ensure that the light sensor operates only when the lamp is on. This operation can reduce the lamp power required for obtaining the UV-Vis spectrum of analytes from about 50 Watt to as low as 2 Watt.

In some embodiments, the light sensor has an entrance slit, a CCD array, and a silicon grating.

In some aspects, the silicon grating can be an etched silicon surface. The silicon grating can have a convex shape for providing a flat focal plane to match the plane of the CCD array.

In general, a CCD (Charge-coupled device) array can detect many wavelengths of light at the same time. Among other things, the small physical size of the light sensor of an apparatus of this invention allows the physical size of the apparatus to be reduced.

Using a CCD detector advantageously allows acquisition of a wide range of wavelengths at the same time without changing the angle of the grating.

In some embodiments, detector overall volume and detector overall power consumption can each be reduced by at least a factor of ten-fold.

In further aspects, an HPLC apparatus of this invention can include a lamp controller microcomputer. The lamp source will in general operate in pulsed mode. Using the lamp controller, the excitation light from the lamp can be synchronized to the data acquisition of the light sensor. By synchronizing the data acquisition, data is acquired only when the lamp is on during a flash process.

By synchronizing the emission of the flash lamp to the light sensor detecting period, an apparatus of this invention advantageously provides the high peak power emission of the flash lamp for detecting analytes.

Referring to FIG. 1, a liquid chromatography apparatus of this invention can include two or more pumps 10, pressure transducers 20, a flow meter 30, a solvent mixer 35, actuated carrier valve 40, actuated sample valve 50, a sample injector 60, carrier reservoirs 70, a detector device 80, a column 90, and a microcomputer controller.

An embodiment of a liquid chromatography apparatus of this invention can include two linear stepping pumps 10 to create pump head pressure on the carrier solvent. By using two stepping pumps, the pump system can be operated in isocratic or differential pumping modes.

The flow system of carrier tubes is used to transfer, mix, and purge carrier liquids, as well as to provide feedback to the pump system. The feedback to the pumps can be provided by pressure transducers 20 and a flow meter 30. The feedback can be used to control the carrier flow speed and pressure. The feedback control can maintain a steady, continuous carrier flow speed and pressure.

The flow system of carrier tubes can be placed in fluid communication using multi-direction actuated switch valves. The actuated carrier valve 40 operates the preparation loop. The actuated sample valve 50 operates the sample loop.

The same or different carrier liquids can be maintained in separate carrier reservoirs 70. The analyte sample, which may contain the same or different carrier liquid as in the pumps, can be injected into the flowing carrier using the sample injector 60. The flowing carrier can carry the sample into the column 90, which is packed with a particle stationary phase suitable for chromatographic retention and analyte separation. The carrier brings the separated analytes to the detector device 80 for analysis. The detector device 80 can detect the separated analyte fractions.

Figure 2:
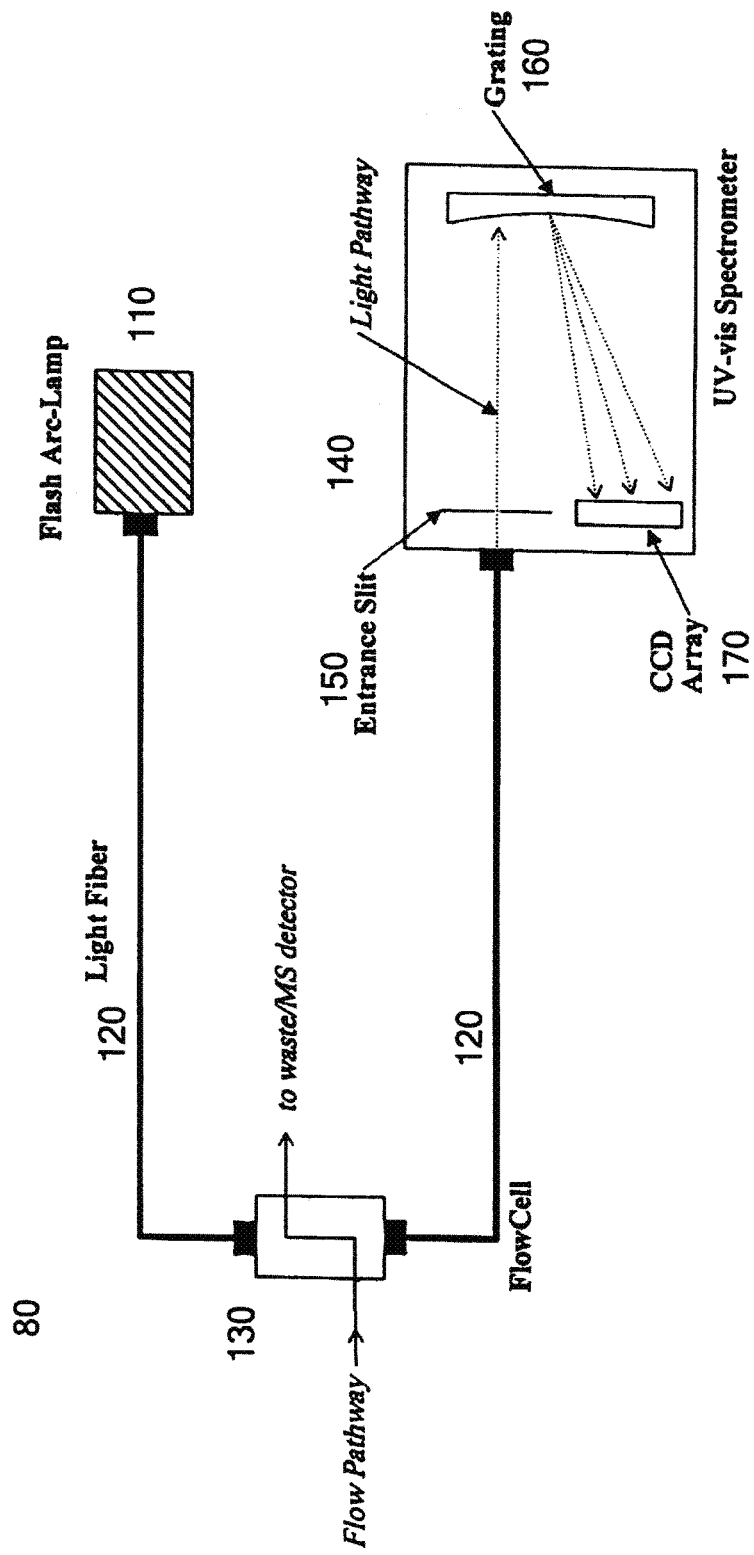
FIG. 2.

Referring to FIG. 2, an embodiment of a detector device 80 of this invention can include a flash lamp 110, light fibers 120, a flow cell 130, and a UV-Vis light sensor 140. The UV-Vis light sensor 140 can include an entrance slit 150, a grating 160, and a CCD array 170.

An embodiment of a liquid chromatography apparatus of this invention can also include a microcomputer controller that can synchronize the operation of the flash lamp to the data acquisition of the light sensor.

With this arrangement, a liquid chromatography apparatus of this invention can provide a high light intensity for detecting analytes. Further, constant pumping speed can be maintained.

A liquid chromatography apparatus of this invention can advantageously use commercial chromatography columns.

A liquid chromatography apparatus of this invention can advantageously be used in the field to for detecting analytes, chemicals, contaminants or other species at their source.

This invention provides the advantageous result that even with reduced mass, a liquid chromatography apparatus of this invention can provide retention times for analytes that remain surprisingly constant. This invention can provide surprisingly accurate quantitative measurements even with reduced mass.

In some embodiments, the carrier tubes in the apparatus were $\frac{1}{16}$" and $\frac{1}{32}$" outer-diameter (OD), 150 micrometer (um) inner-diameter (ID) Polytetrafluoroethylene (PTFE) tubes in channel A and 25 um ID PTFE tubes in channel B, preparation loop.

A six-direction switch valve, for example, C52-1006I (Valco), could be used for each of the preparation and sample loops.

Example pressure transducers include DF2-SS-01-10K (DJ instruments).

Example flow sensors include SLG1430 (CMOSens Technology).

In certain embodiments, an HPLC apparatus of this invention can be compatible with $\frac{1}{16}$" or $\frac{1}{32}$" or 380 um OD HPLC columns.

In further aspects, an apparatus of this disclosure can have the ability to separate various unknown samples by replacing the column with one or more different columns.

In certain embodiments, a detector device can include a scan range of from 230 nm to 800 nm.

In further embodiments, an HPLC apparatus of this invention can be connected to a mass spectrometer, a nuclear magnetic resonance spectrometer, or a light scattering detector.

In one embodiment, an HPLC apparatus of this invention was made having a mass of less than 12 kg and a volume of less than 22 L. This apparatus had overall power consumption of less than 200 W and was operated using a lithium-ion battery. The apparatus can optionally be powered with conventional electrical power sources.

In one embodiment, a detector device for an HPLC apparatus of this invention was made having power consumption of 2 W and overall size of 0.486 liter (9 cm by 18 cm by 3 cm).

A liquid chromatography apparatus of this invention can advantageously provide high-throughput screening and detecting of analytes in combination with an efficient, small volume mass spectrometer. When the power consumption and volume of both the LC apparatus and the mass spectrometer apparatus are reduced, the combination is capable of high throughput detection of analytes as compared to a conventional LC-MS apparatus.

Further, a liquid chromatography apparatus of this invention can advantageously be used in a patient clinic.

Also, a liquid chromatography apparatus of this invention can advantageously be used for environmental measurements in the field or at remote locations to detect analytes, chemicals, contaminants or other species at their source.

Example 1

Figure 3:
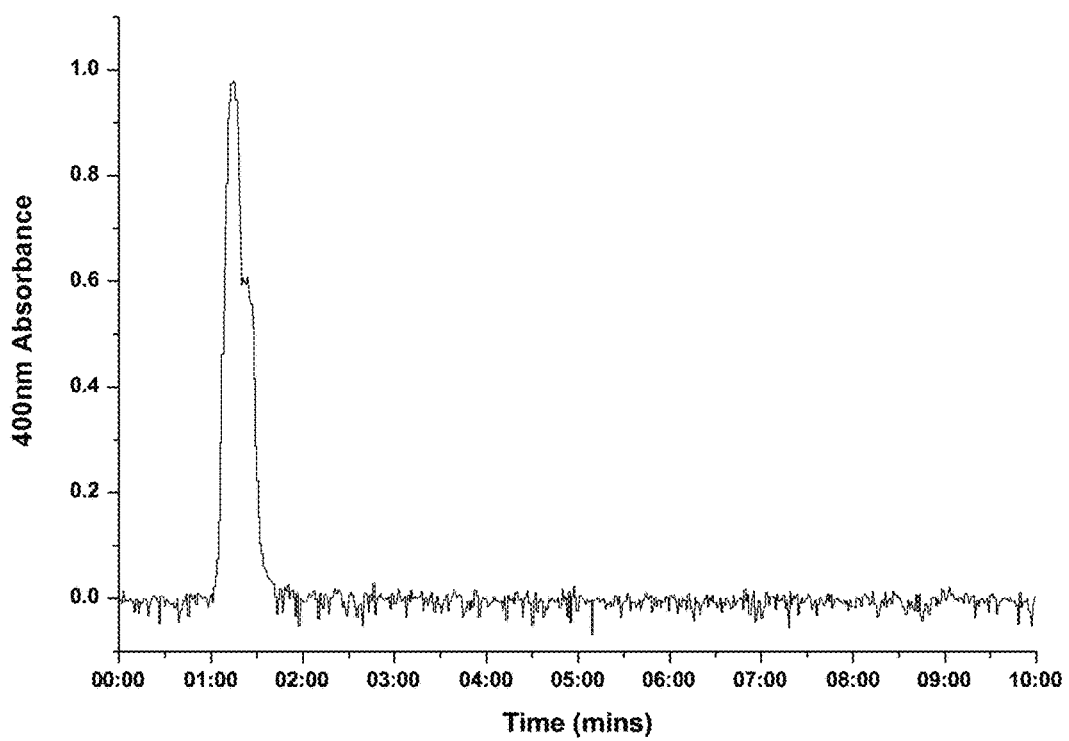
FIG. 3.

An HPLC of this invention was assembled having a UV-Vis detector device. The HPLC had less than 10 L total volume. This HPLC was operated with less than 150 Watt overall power consumption. Referring to FIG. 3, a chromatogram showing retention time versus absorbance was obtained with this HPLC for a sample of MyoGlobin. Absorbance was obtained at 400 nm wavelength.

All publications and patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A method for performing liquid chromatography, the method comprising:
   providing analytes in a carrier liquid, the carrier liquid being an organic solvent;
   step-pumping the carrier liquid through a chromatography column to separate the analytes using two linearly-driven ball screw piston stepping pumps and feedback from a pressure transducer and a flow meter to maintain a steady, continuous carrier flow speed and pressure up to $1.4 \times 10^8$ Pa, wherein a shaft of the stepper motor directly drives its piston to generate a stroke;
   switching from sample loading to sample loop without high pressure injection to the column;
   detecting the separated analytes with a detector device comprising a flash lamp and a UV-Visible light sensor which operates only when the lamp is on, a separate flow cell coupled to the flash lamp and light sensor, the light sensor comprising a grating for impinging light from 230 to 800 nm wavelength directly onto a charge-coupled device array, to measure absorbance of a specific bandwidth of the light, without the use of a monochromator and/or light filter, wherein the analytes detected are compounds having a characteristic of light absorption/emission and non-emissive compounds.

2. The method of claim 1, wherein the grating is an etched silicon light diffraction grating having convex shape for focusing diffracted light.

3. The method of claim 1, wherein the chromatography column is selected from an adsorption, a partition, an ion exchange, an affinity, and a size exclusion retention column.

4. The method of claim 1, wherein the detector device has a scan range of from 230 nm to 800 nm.

5. The method of claim 1, wherein the step-pumping has a minimum step of 0.8 nanoliter.

6. The method of claim 1, wherein the flash lamp is operated at a power of 2 Watt.

7. The method of claim 1, further comprising operating a microcomputer controller to synchronize the operation of the flash lamp to the operation of the charge-coupled device array.

8. The method of claim 1, further comprising focusing diffracted light from the grating onto the charge-coupled device array.

* * * * *